US006410269B1

(12) United States Patent
Yamamoto

(10) Patent No.: US 6,410,269 B1
(45) Date of Patent: Jun. 25, 2002

(54) PREPARATION OF POTENT MACROPHAGE ACTIVATING FACTORS DERIVED FROM CLONED VITAMIN D BINDING PROTEIN AND ITS DOMAIN AND THEIR THERAPEUTIC USAGE FOR CANCER, HIV-INFECTION AND OSTEOPETROSIS

(76) Inventor: Nobuto Yamamoto, 1040 66th Ave., Philadelphia, PA (US) 19126

( * ) Notice: Subject to any disclaimer, the term of this patent is extended or adjusted under 35 U.S.C. 154(b) by 970 days.

(21) Appl. No.: 08/618,485

(22) Filed: Mar. 19, 1996

Related U.S. Application Data

(63) Continuation-in-part of application No. 08/478,121, filed on Jun. 7, 1995, now Pat. No. 5,620,846.
(51) Int. Cl.⁷ .................. C12P 21/00; C12N 15/00; C07K 14/46
(52) U.S. Cl. ................ 435/69.6; 435/68.1; 435/320.1; 435/174; 530/300; 530/395
(58) Field of Search ............................. 435/69.6, 68.1, 435/320.1, 174; 530/300, 395

(56) References Cited

U.S. PATENT DOCUMENTS

| | | | |
|---|---|---|---|
| 5,177,001 A | | 1/1993 | Yamamoto .................. 435/68.1 |
| 5,177,002 A | * | 1/1993 | Yamamoto .................. 435/68.1 |
| 5,326,749 A | | 7/1994 | Yamamoto ..................... 514/8 |

OTHER PUBLICATIONS

Luckow VA. Protein production and processing from baculovirus expression vectors. In, Insect Cell Cultures: Biopesticide and Protein Production, Shuler ML; Granados, RR; Hammer, DA; Woods, HA (eds.), John Wiley and Sons, 1993.*

Genomics, vol. 16, issued 1993, Witke et al., "Complet Structure of the Human Gc Gene: Differences and Similarities Between Members of the Albumin Gene Family", pp. 751–754 see entire document.

Biochimica et Biophysica Acta, vol. 1216, issued 1993, Braun et al., "Sequence and Organization of the Human Vitamin D Binding Protein Gene", pp. 385–394, see entire document.

Proceedings of the National Academy of Science, U.S.A., vol. 82, issue Dec. 1985, Yang et al. "Human Group–Specifi Component (Gc) is a Member of the Albumin Family", pp. 7994–7998, see entire document.

Biochemica et Biophysica Acta, vol. 871, issued 1986 Schoentgen et al., "Complete Amino Acid Sequence of Huma Vitamin D–Binding Protein (Group-Specific Component): Evidence of a Three–fold Internal Homology as a Serum Albumin an alpha–Fetoprotein", pp. 189–198, see entire document.

Yamamoto, N. and Homma, S., Vitamin $D_3$ binding protein (group–specific component is a precursor for the macrophage activating signal from lysophosphatidylcholine–treated lymphocytes. Proc. Natl. Acad. Sci. USA, vol. 88, pp. 8539–8543 (1991).

Yamamoto, N. and Kumashiro, R., Conversion of vitamin $D_3$ binding protein (Group–specific component) to a macrophage activating factor by stepwise action of β–galactosidase of B cells and sialidase of T cells. J. Immunol. 151:2794–2902 (1993).

Ngwenya, B.Z., and Yamamoto, N., Activation of peritoneal macrophages by lysophosphatidylcholine. Biochem. Biophys. Acta 839: 9–15 (1985).

Ngwenya, B.Z. and Yamamoto, N., Contribution of lysophosphatidylcholine treated nonadherent cells to mechanism of macrophage stimulation. Proc. Soc. Exp. Biol. Med. 193:118–124 (1990).

Homma, S., Yamamoto, M. and Yamamoto, N., Vitamin D binding protein (group–specific componenT, Gc) is the sole serum protein required for macrophage activation after treatment of peritoneal cells with lysophosphatidylcholine. Immunol. Cell Biol. 71:249–257 (1993).

Yamamoto, N., Kumashiro, R., Yamamoto, M., Willett, N. P. and Lindsay, D.D., Regulation of inflammation–primed activation of macrophages by two serum factors, vitamin $D_3$–binding protein and albumin. Inf. Imm. 61:5388–5391 (1993).

Yamamoto, N., Lindsay, D. D., Naraparaju, V. R., Irelalnd, R. A. and Popoff, S.M., A defect in the inflammation–primed macrophage activation cascade in osteopetrotic (op) rats. J. Immunol. 152:5100–5107 (1994).

Yamamoto, N., Willett, N.P. and Lindsay, D.D., Participation of serum proteins in the inflammation–primed activation of macrophages. Inflammation. 18:311–322 (1994).

Naraparaju, V.R. and Yamamoto, N., Roles of β–galactosidase of B lymphocytes and sialidase of T lymphocytes in inflammation–primed activation of macrophages. Immunol. Lett. 43:143–148 (1994).

(List continued on next page.)

Primary Examiner—David S. Romeo
(74) Attorney, Agent, or Firm—Caesar, Rivise, Bernstein, Cohen, & Pokotilow, Ltd.

(57) ABSTRACT

Vitamin D-binding protein (Gc protein) and its small domain (approximately ⅓ of the Gc peptide also known as domain III) were cloned via a baculovirus vector. The cloned Gc protein and the cloned domain (Cd) peptide were treated with immobilized β-galactosidase and sialidase to yield macrophage activating factors, GcMAFc and CdMAF, respectively. These cloned macrophage activating factors and GcMAF are to be used for therapy of cancer, HIV-infection and osteopetrosis, and may also be used as adjuvants for immunization and vaccination.

6 Claims, 11 Drawing Sheets

OTHER PUBLICATIONS

Yamamoto, N., Naraparaju, V.R. and Srinivasula, S.M., Structural modification of serum vitamin $D_3$–binding protein and immunosuppression in HIV–infected patients. AIDS Res. Human Ret. 11:1373–1378 (1995).

Sato, M., Tanaka, H., Yamada, T. and Yamamoto, N., Persistent infection of BHK/WI–2 cells with rubella virus and characterization of rubella variants. Arch. Virology 54:333–343 (1977).

Cooke, N.E and David, E.V., Serum Vitamin D–binding Protein is a Third Member of the Albumin and Alpha Fetoprotein Gene Family. J. Clin. Invest., Inc. vol. 76, Dec. 1985, 2420–2424.

* cited by examiner

```
                                      10                                          20
Leu Glu Arg Gly Arg Asp Tyr  Glu  Lys Asn Lys Val Cys Lys Glu Phe  Ser  His  Leu Gly
                                      30                                          40
Lys Glu Asp phe Thr Ser Leu Ser Leu Val Leu Tyr Ser Arg Lys Phe Pro Ser Gly Thr
                                      50                                          60
Phe Glu Gln Val Ser Gln Leu Val Lys Glu Val Val Ser Leu Thr Glu Ala Cys Cys Ala
                                      70                                          80
Glu Gly Ala Asp Pro Asp Cys Tyr Asp Thr Arg Thr Ser Ala Leu Ser Ala Lys Ser Cys
                                      90                                          100
Glu Ser Asn Ser Pro Phe Pro Val His Pro Gly Thr Ala Glu Cys Cys Thr Lys Glu Gly
                                      110                                         120
Leu Glu Arg Lys Leu Cys Met Ala Ala Leu Lys His Gln Pro Gln Glu Phe Pro Thr Tyr
                                      130                                         140
Val Glu Pro Thr Asn Asp Glu Ile Cys Glu Ala Phe Arg Lys Asp Pro Lys GLu Tyr Ala
                                      150                                         160
Asn Gln Phe Met Trp Glu Tyr Ser Thr Asn Tyr Glu Gln Ala Pro Leu Ser Leu Leu Val
                                      170                                         180
Ser Tyr Thr Lys Ser Tyr Leu Ser Met Val Gly Ser Cys Cys Thr Ser Ala Ser Pro Thr
                                      190                                         200
Val Cys Phe Leu Lys Glu Arg Leu Gln Leu Lys His Leu Ser Leu Leu Thr Thr Leu Ser
                                      210                                         220
Asn Arg Val Cys Ser Gln Tyr Ala Ala Tyr Gly Glu Lys Lys Ser Arg Leu Ser Asn Leu
                                      230                                         240
Ile Lys Leu Ala Gln Lys Val Pro Thr Ala Asp Leu Glu Asp Val Leu Pro Leu Ala Glu
                                      250                                         260
Asp Ile Thr Asn Ile Leu Ser Lys Cys Cys Glu Ser Ala Ser Glu Asp Cys Met Ala Lys
                                      270                                         280
Glu Leu Pro Glu His Thr Val Lys Leu Cys Asp Asn Leu Ser Thr Lys Asn Ser Lys Phe
                                      290                                         300
Glu Asp Cys Cys Gln Glu Lys Thr Ala Met Asp Val Phe Val Cys Thr Tyr Phe Met Pro
                                      310                                         320
Ala Ala Gln Leu Pro Glu Leu Pro Asp Val Arg Leu Pro Thr Asn Lys Asp Val Cys Asp
                                      330                                         340
Pro Gly Asn Thr Lys Val Met Asp Lys Tyr Thr Phe Glu Leu Ser Arg Arg Thr His Leu
                                      350                                         360
Pro Glu Val Phe Leu Ser Lys Val Leu Glu Pro Thr Leu Lys Ser Leu Gly Glu Cys Cys
                                      370                                         380
Asp Val Glu Asp Ser Thr Thr Cys phe Asn Ala Lys Gly Pro Leu Leu Lys Lys Glu Leu
                                      390                                         400
Ser Ser Phe Ile Asp Lys Gly Gln Glu Leu Cys Ala Asp Tyr Ser Glu Asn Thr Phe Thr
                                      410                                         420
Glu Tyr Lys Lys Lys Leu Ala GlU Arg Leu Lys Ala Lys Leu Pro Glu Ala Thr Pro Thr
                                      430                                         440
Glu Leu Ala Lys Leu Val Asn Lys Arg Ser Asp Phe Ala Ser Asn Cys Cys Ser Ile Asn
                                      450                                         458
Ser Pro Pro Leu Tyr Cys Asp Ser Glu Ile Asp Ala Glu Leu Lys Asn Ile Leu
```

FIG. 3

```
Leu Glu Arg Gly Pro Leu Leu Lys Lys Glu Leu Ser Ser Phe Ile Asp Lys Gly Gln Glu
                                    10                                        20
Leu Cys Ala Asp Tyr Ser Glu Asn Thr Phe Thr Glu Tyr Lys Lys Leu Ala Glu Arg
                                    30                                    40
Leu Lys Ala Lys Leu Pro Glu Ala Thr Pro Thr Glu Leu Ala Lys Leu Val Asn Lys Arg
                                    50                                        60
Ser Asp Phe Ala Ser Asn Cys Cys Ser Ile Asn Ser Pro Pro Leu Tyr Cys Asp Ser Glu
                                    70                                        80
Ile Asp Ala Glu Leu Lys Asn Ile Leu
                        89
```

```
                                          10                           20
  Ile Ile Pro Val Glu Glu Glu Asn Pro Pro Leu Leu Lys Lys Glu Leu Ser Ser Phe Ile
                      30                           40
  Asp Lys Gly Gln Glu Leu Cys Ala Asp Tyr Ser Glu Asn Thr Phe Thr Glu Tyr Lys
                      50                           60
  Lys Leu Ala Glu Arg Leu Lys Ala Lys Leu Pro Glu Ala Thr Pro Thr Glu Leu Ala Lys
                      70                           80
  Leu Val Asn Lys Arg Ser Asp Phe Ala Ser Asn Cys Cys Ser Ile Asn Ser Pro Pro Leu
                      90      94
  Tyr Cys Asp Ser Glu Ile Asp Ala Glu Leu Lys Asn Ile Leu
```

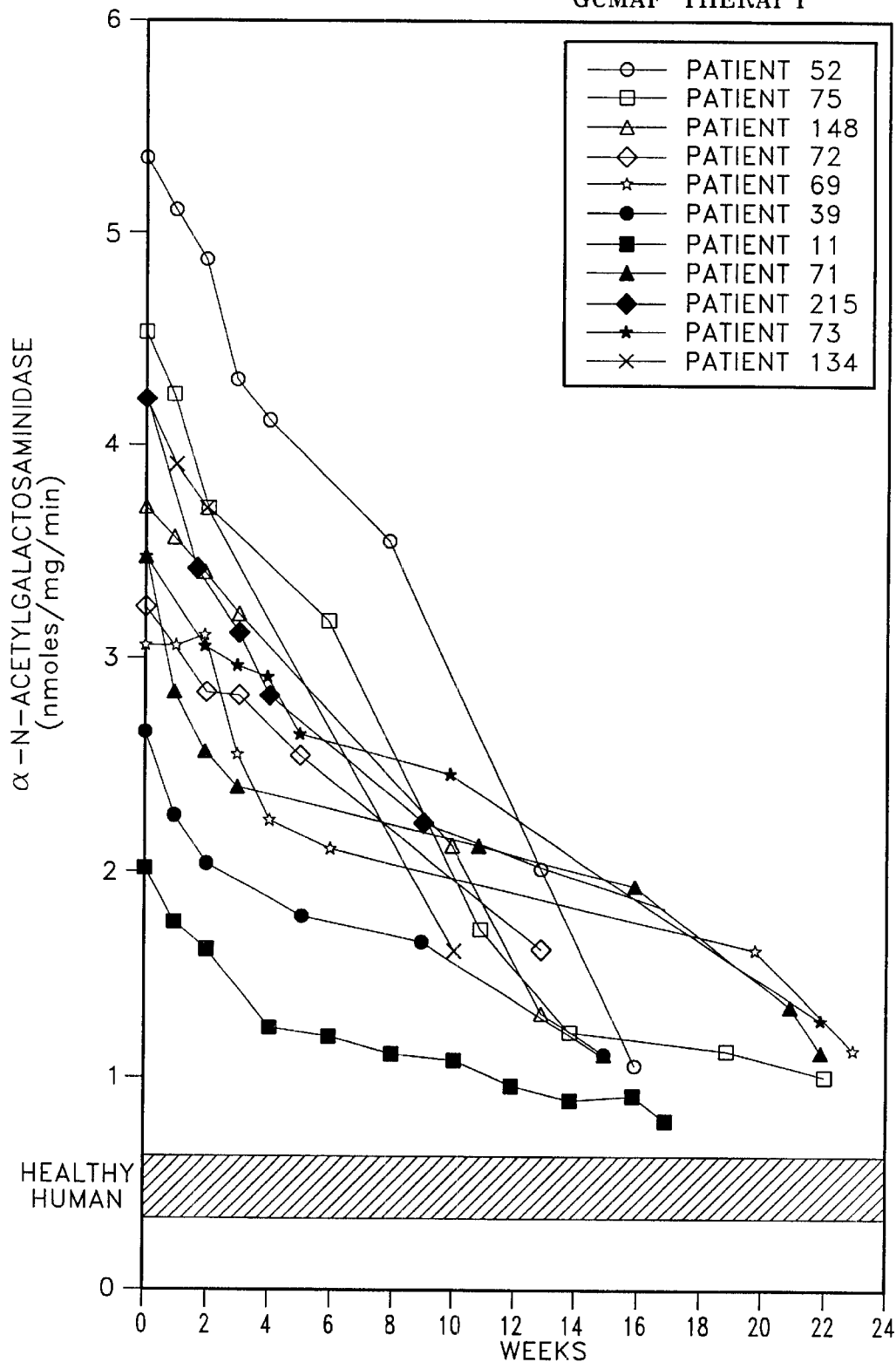

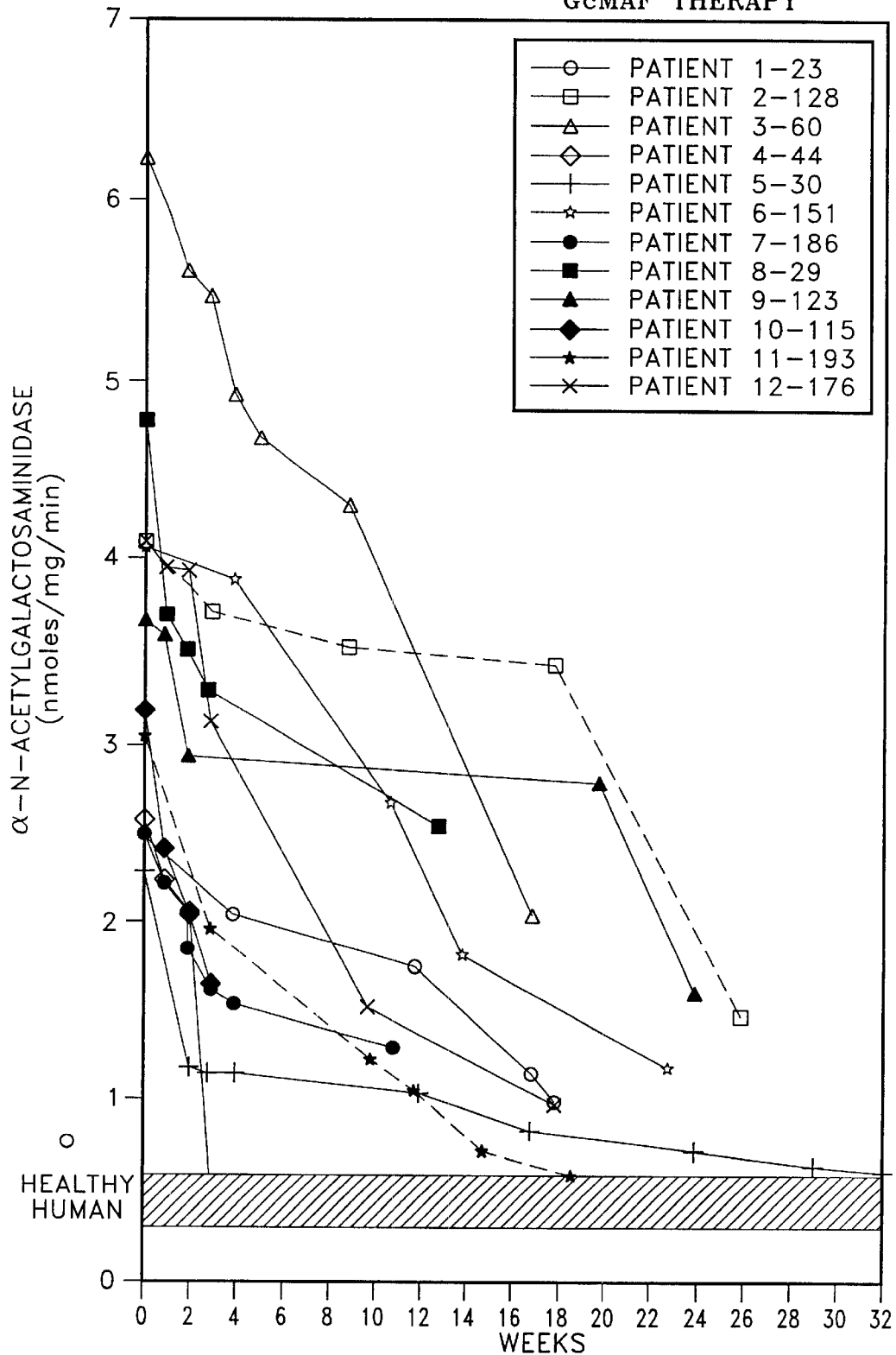
FIG. 8B BREAST CANCER GcMAF THERAPY

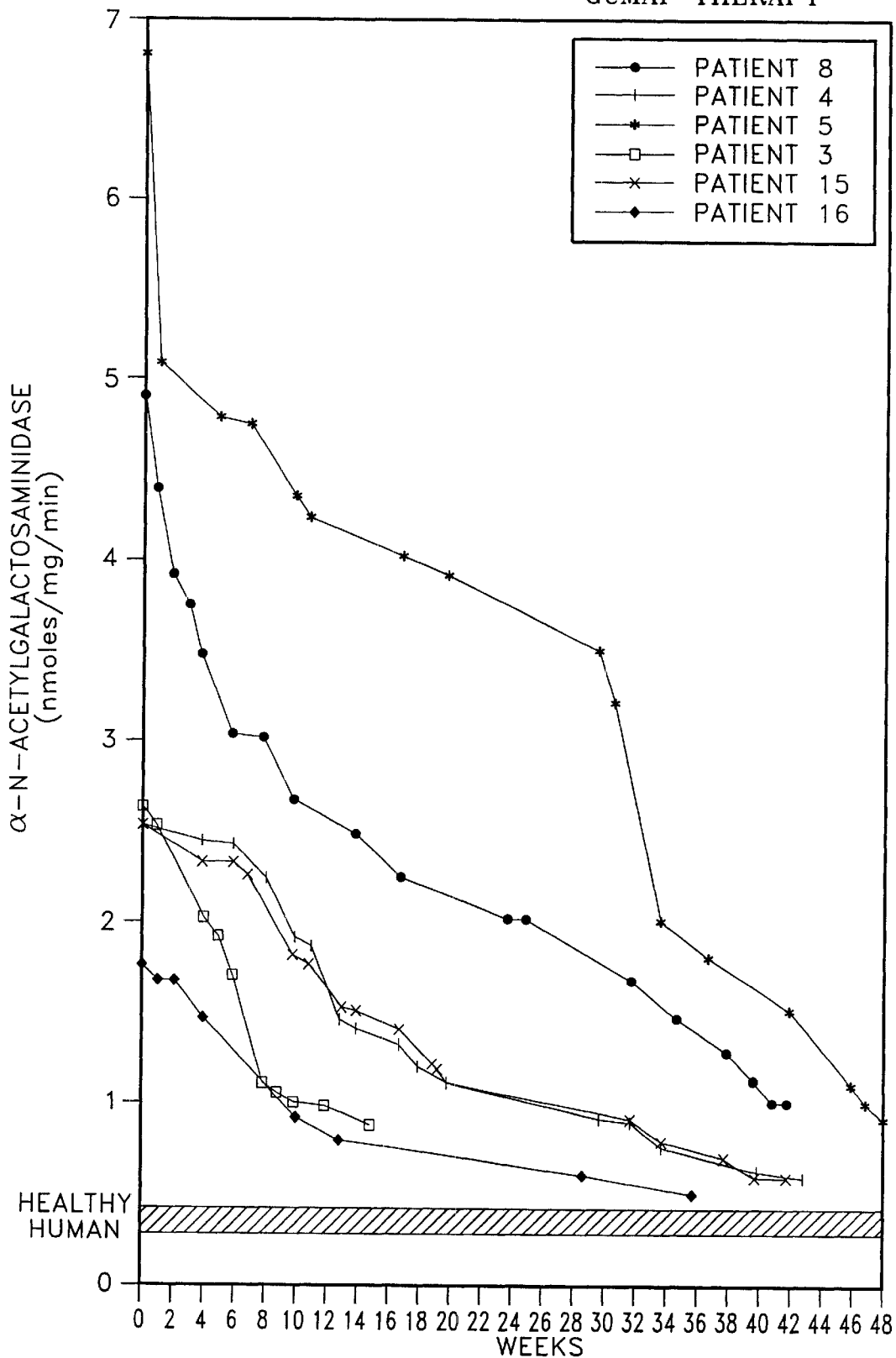
FIG. 8C COLON CANCER GcMAF THERAPY

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 458 amino acids
      (B) TYPE: amino acid
      (D) TOPOLOGY: linear (ii) MOLECULE TYPE: protein (ii) HYPOTHETICAL: no (vi) ORIGINAL SOURCE:
      (A) ORGANISM: Human
      (B) INDIVIDUAL ISOLATE: Vitamin D-binding protein (Gc protein)

(x) PUBLICATION INFORMATION:
      (A) AUTHORS: Cooke, Nancy E., David, E Vivek
      (B) TITLE: Serum Vitamin D-binding Protein is a Third Member of the Albumin and Alpha Fetoprotein Gene Family
      (C) JOURNAL: J. Clinical Investigation
      (D) VOLUME: 76
      (E) ISSUE: 12
      (F) PAGES: 2420-2424
      (G) DATE: December, 1985
      (K) RELEVANT RESIDUES IN SEQ ID NO:1: FROM 1-485

(xi) SEQUENCE DESCRIPTION: SEQ ID NO:1:

```
Leu Glu Arg Gly Arg Asp Tyr Glu Lys Asn Lys Val Cys Lys Glu Phe
                  5                  10                  15

Ser His Leu Gly Lys Glu Asp Phe Thr Ser Leu Ser Leu Val Leu Tyr
                 20                  25                  30

Ser Arg Lys Phe Pro Ser Gly Thr Phe Glu Gln Val Ser Gln Leu Val
                 35                  40                  45

Lys Glu Val Val Ser Leu Thr Glu Ala Cys Cys Ala Glu Gly Ala Asp
 50                  55                  60

Pro Asp Cys Tyr Asp Thr Arg Thr Ser Ala Leu Ser Ala Lys Ser Cys
 65                  70                  75                  80

Glu Ser Asn Ser Pro Phe Pro Val His Pro Gly Thr Ala Glu Cys Cys
                 85                  90                  95

Thr Lys Glu Gly Leu Glu Arg Lys Leu Cys Met Ala Ala Leu Lys His
                100                 105                 110

Gln Pro Gln Glu Phe Pro Thr Tyr Val Glu Pro Thr Asn Asp Glu Ile
                115                 120                 125

Cys Glu Ala Phe Arg Lys Asp Pro Lys Glu Tyr Ala Asn Gln Phe Met
130                 135                 140

Trp Glu Tyr Ser Thr Asn Tyr Gly Gln Ala Pro Leu Ser Leu Leu Val
145                 150                 155                 160

Ser Tyr Thr Lys Ser Tyr Leu Ser Met Val Gly Ser Cys Cys Thr Ser
                165                 170                 175

Ala Ser Pro Thr Val Cys Phe Leu Lys Glu Arg Leu Gln Leu Lys His
                180                 185                 190
```

```
Leu Ser Leu Leu Thr Thr Leu Ser Asn Arg Val Cys Ser Gln Tyr Ala
            195                 200                 205
Ala Tyr Gly Glu Lys Lys Ser Arg Leu Ser Asn Leu Ile Lys Leu Ala
    210                 215                 220
Gln Lys Val Pro Thr Ala Asp Leu Glu Asp Val Leu Pro Leu Ala Glu
225                 230                 235                 240
Asp Ile Thr Asn Ile Leu Ser Lys Cys Cys Glu Ser Ala Ser Glu Asp
                245                 250                 255
Cys Met Ala Lys Glu Leu Pro Glu His Thr Val Lys Leu Cys Asp Asn
            260                 265                 270
Leu Ser Thr Lys Asn Ser Lys Phe Glu Asp Cys Cys Gln Glu Lys Thr
        275                 280                 285
Ala Met Asp Val Phe Val Cys Thr Tyr Phe Met Pro Ala Ala Gln Leu
    290                 295                 300
Pro Glu Leu Pro Asp Val Arg Leu Pro Thr Asn Lys Asp Val Cys Asp
305                 310                 315                 320
Pro Gly Asn Thr Lys Val Met Asp Lys Tyr Thr Phe Glu Leu Ser Arg
                325                 330                 335
Arg Thr His Leu Pro Glu Val Phe Leu Ser Lys Val Leu Glu Pro Thr
            340                 345                 350
Leu Lys Ser Leu Gly Glu Cys Cys Asp Val Glu Asp Ser Thr Thr Cys
        355                 360                 365
Phe Asn Ala Lys Gly Pro Leu Leu Lys Lys Glu Leu Ser Ser Phe Ile
    370                 375                 380
Asp Lys Gly Gln Glu Leu Cys Ala Asp Tyr Ser Glu Asn Thr Phe Thr
385                 390                 395                 400
Glu Tyr Lys Lys Lys Leu Ala Glu Arg Leu Lys Ala Lys Leu Pro Glu
                405                 410                 415
Ala Thr Pro Thr Glu Leu Ala Lys Leu Val Asn Lys Arg Ser Asp Phe
            420                 425                 430
Ala Ser Asn Cys Cys Ser Ile Asn Ser Pro Pro Leu Tyr Cys Asp Ser
        435                 440                 445
Glu Ile Asp Ala Glu Leu Lys Asn Ile Leu
    450                 455         458

(2) INFORMATION FOR SEQ ID NO: 2:

(i) SEQUENCE CHARACTERISTICS:
        (A) LENGTH: 89 amino acids
        (B) TYPE: amino acid
        (D) TOPOLOGY: linear (ii) MOLECULE TYPE: protein (ii) HYPOTHETICAL: no (vi) ORIGINAL SOURCE:
        (A) ORGANISM: Human
        (B) INDIVIDUAL ISOLATE: Vitamin D-binding protein (Gc protein)

(x) PUBLICATION INFORMATION:
        (A) AUTHORS: Cooke, Nancy E., David, E Vivek
        (B) TITLE: Serum Vitamin D-binding Protein is a Third Member
            of the Albumin and Alpha Fetoprotein Gene Family
        (C) JOURNAL: J. Clinical Investigation
        (D) VOLUME: 76
        (E) ISSUE: 12
        (F) PAGES: 2420-2424
        (G) DATE: December, 1985
        (K) RELEVANT RESIDUES IN SEQ ID NO:2: FROM 1 TO 4 and 5 TO 89
```

(xi) SEQUENCE DESCRIPTION: SEQ ID NO:2:

Leu Glu Arg Gly Pro Leu Leu Lys Lys Glu Leu Ser Ser Phe Ile Asp
                5                   10                  15

Lys Gly Gln Glu Leu Cys Ala Asp Tyr Ser Glu Asn Thr Phe Thr Glu
                20                  25                  30

Tyr Lys Lys Lys Leu Ala Glu Arg Leu Lys Ala Lys Leu Pro Glu Ala
                35                  40                  45

Thr Pro Thr Glu Leu Ala Lys Leu Val Asn Lys Arg Ser Asp Phe Ala
    50                  55                  60

Ser Asn Cys Cys Ser Ile Asn Ser Pro Pro Leu Tyr Cys Asp Ser Glu
65                  70                  75                  80

Ile Asp Ala Glu Leu Lys Asn Ile Leu
                85                  89

(2) INFORMATION FOR SEQ ID NO: 3:

(i) SEQUENCE CHARACTERISTICS:
        (A) LENGTH: 94 amino acids
        (B) TYPE: amino acid
        (D) TOPOLOGY: linear (ii) MOLECULE TYPE: protein (ii) HYPOTHETICAL: no (vi) ORIGINAL SOURCE:
        (A) ORGANISM: Human
        (B) INDIVIDUAL ISOLATE: Vitamin D-binding protein (Gc protein)

(x) PUBLICATION INFORMATION:
        (A) AUTHORS: Cooke, Nancy E., David, E Vivek
        (B) TITLE: Serum Vitamin D-binding Protein is a Third Member
            of the Albumin and Alpha Fetoprotein Gene Family
        (C) JOURNAL: J. Clinical Investigation
        (D) VOLUME: 76
        (E) ISSUE: 12
        (F) PAGES: 2420-2424
        (G) DATE: December, 1985
        (K) RELEVANT RESIDUES IN SEQ ID NO:3: FROM 10 TO 94

(xi) SEQUENCE DESCRIPTION: SEQ ID NO:3:

Ile Ile Pro Val Glu Glu Glu Asn Pro Pro Leu Leu Lys Lys Glu Leu
                5                   10                  15

Ser Ser Phe Ile Asp Lys Gly Gln Glu Leu Cys Ala Asp Tyr Ser Glu
                20                  25                  30

Asn Thr Phe Thr Glu Tyr Lys Lys Lys Leu Ala Glu Arg Leu Lys Ala
                35                  40                  45

Lys Leu Pro Glu Ala Thr Pro Thr Glu Leu Ala Lys Leu Val Asn Lys
    50                  55                  60

Arg Ser Asp Phe Ala Ser Asn Cys Cys Ser Ile Asn Ser Pro Pro Leu
65                  70                  75                  80

Tyr Cys Asp Ser Glu Ile Asp Ala Glu Leu Lys Asn Ile Leu
                85                  90                  94

PREPARATION OF POTENT MACROPHAGE ACTIVATING FACTORS DERIVED FROM CLONED VITAMIN D BINDING PROTEIN AND ITS DOMAIN AND THEIR THERAPEUTIC USAGE FOR CANCER, HIV-INFECTION AND OSTEOPETROSIS

RELATED APPLICATIONS

This application is a continuation-in-part application of ASN 08/478,121, now U.S. Pat. No. 5,620,846, filed Jun. 7, 1995, entitled DIAGNOSTIC AND PROGNOSTIC INDICES FOR CANCER AND AIDS, the entire disclosure of which is incorporated by reference herein.

FIELD OF THE INVENTION

This invention relates to potent macrophage activating factors, prepared by oligosaccharide digestion of the cloned vitamin D binding protein (Gc protein) and the cloned Gc protein domain III, and the use of these macrophage activating factors for various cancer, HIV-infection and osteopetrosis, and as adjuvants for immunization and vaccination.

TABLE OF TERMS

| | |
|---|---|
| Gc protein | Vitamin $D_3$-binding protein |
| MAF | macrophage activating factor |
| GcMAF | Gc protein-derived macrophage activating protein |
| GcMAFc | cloned Gc protein-derived macrophage activating factor |
| Gc domain III | domain III region of Gc protein |
| CdMAF | cloned domain III-derived macrophage activating factor |

SUMMARY OF THE INVENTION

Vitamin D-binding protein (Gc protein) and its small domain (approximately ⅕ of the Gc peptide also known as domain III) were cloned via a baculovirus vector. The cloned Gc protein and the cloned domain (Cd) peptide were treated with immobilized β-galactosidase and sialidase to yield macrophage activating factors, GcMAFc and CdMAF, respectively. These cloned macrophage activating factors and GcMAF are to be used for therapy of cancer, HIV-infection and osteopetrosis, and may also be used as adjuvants for immunization and vaccination.

DESCRIPTION OF THE DRAWINGS

Other objects and many attendant features of this invention will become readily appreciated as the same becomes better understood by reference to the following detailed description when considered in connection with the accompanying drawings wherein:

FIG. 3 shows the amino acid sequence of cloned GcMAF which is SEQ ID NO:1 which is the entire cloned Gc protein.

FIG. 5 shows the 89 amino acid sequence, SEQ ID NO:2, of the cloned domain III ($CdMAF_1$), using the non-fusion vector.

FIG. 7 shows the 94 amino acid sequence, SEQ ID NO:3, of the cloned domain III ($CdMAF_2$), using the fusion vector.

FIG. 8a shows the therapeutic effect of GcMAF in accordance with the present invention on adult persons suffering from prostate cancer.

FIG. 8b shows the therapeutic effect of GcMAF in accordance with the present invention on adult persons suffering from breast cancer.

FIG. 8c shows the therapeutic effect of GcMAF in accordance with the present invention on adult persons suffering from colon cancer.

BACKGROUND OF THE INVENTION

A. Inflammatory Response Results In Activation of Macrophages

Inflammation results in the activation of macrophages. Inflamed lesions release lysophospholipids. The administration into mice of small doses (5–20 μg/mouse) of lysophosphatidylcholine (lyso-Pc) and other lysophospholipids induced a greatly enhanced phagocytic and superoxide generating capacity of macrophages (Ngwenya and Yamamoto, *Proc. Soc. Exp. Biol. Med.* 193:118, 1990; Yamamoto et al., *Inf. Imm.* 61:5388, 1993; Yamamoto et al., *Inflammation.* 18:311, 1994).

Figure 1A:
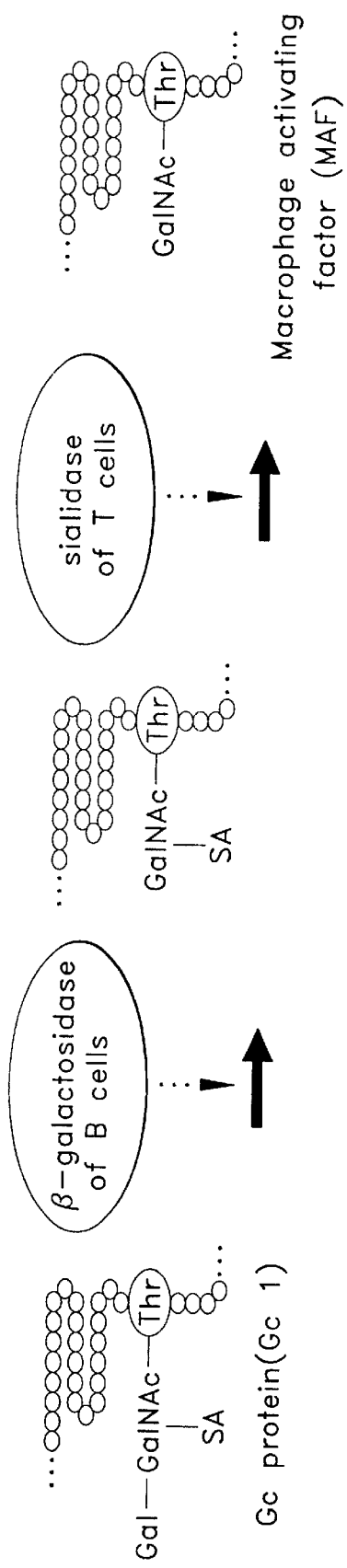
FIG. 1a is a schematic illustration of the formation of macrophage activating factor (MAF).

This macrophage activation requires participation of B and T lymphocytes and serum vitamin D binding protein (DBP; human DBP is known as Gc protein). In vitro activation of mouse peritoneal macrophages by lyso-Pc requires the step-wise modification of Gc protein by β-galactosidase of lyso-Pc-treated B cells and sialidase of T cells to generate the macrophage activating factor (MAF), a protein with N-acetylgalactosamine as the remaining sugar moiety (FIG. 1a) (Yamamoto et al. *Proc. Natl. Acad. Sci. USA.* 88:8589, 1991: Yamamoto et al., *J. Immunol.* 151:2794, 1993; Naraparaju and Yamamoto, *Immunol. Lett.* 43:143, 1994). Thus, Gc protein is a precursor for MAF.

Incubation of Gc protein with immobilized β-galactosidase and sialidase generates a remarkably high titered MAF (GcMAF) (Yamamoto et al., *Proc. Natl. Acad. Sci. USA.* 88:8539, 1991; Yamamoto et al., *J. Immunol.* 151:2794, 1993; Naraparaju and Yamamoto, *Immunol. Lett.* 43:143, 1994; U.S. Pat. No. 5,177,002). Administration of a minute amount (10 pg/mouse; 100 ng/human) of GcMAF resulted in greatly enhanced phagocytic and superoxide generating capacities of macrophages.

Figure 1B:
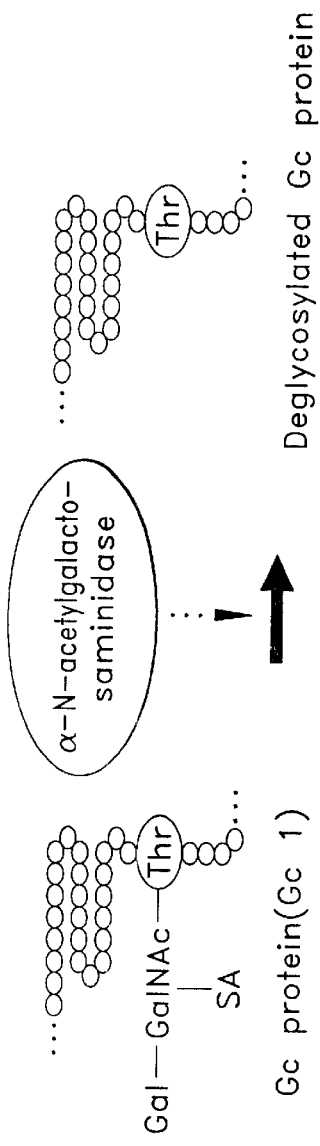
FIG. 1b is a schematic illustration of the deglycosylation of Gc protein in a cancer or HIV-infected patient's blood stream.

When peripheral blood monocytes/macrophages (designated as macrophages hereafter) of 258 cancer patients bearing various types of cancer were treated in vitro with 100 pg GcMAF/ml, macrophages of all cancer patients were activated for phagocytic and superoxide generating capacity. This observation indicates that cancer patient macrophages are capable of being activated. However, the MAF precursor activity of plasma Gc protein was lost or reduced in approximately 70% of this cancer patient population. Loss of the MAF precursor activity prevents generation of MAF. Therefore, macrophage activation cannot develop in certain cancer patients. Since macrophage activation is the first step in the immune development cascade, such cancer patients become immunosuppressed. This may explain at least in part why cancer patients die from overwhelming infection. Lost or reduced precursor activity of Gc protein was found to be due to deglycosylation of plasma Gc protein by α-N-acetylgalactosaminidase detected in cancer patient blood stream. Deglycosylated Gc protein cannot be converted to MAF (FIG. 1b).

Similarly, when peripheral blood macrophages of 160 HIV-infected/AIDS patients were treated in vitro with 100 pg GcMAF/ml, macrophages of all patients were activated for phagocytic and superoxide generating capacity. However, the MAF precursor activity of plasma Gc protein was low in approximately 35% of the HIV-infected patient population. As in cancer patients, these patients' plasma Gc protein is deglycosylated by α-N-acetylgalactosaminidase detected in HIV-infected patients.

Both cancer and HIV-infected patients having severely decreased precursor activity of plasma Gc protein carried large amounts of α-N-acetylgalactosaminidase while patients having moderately decreased precursor activity had moderate levels of plasma α-N-acetylgalactosaminidase activities. Patients with high precursor activity, including asymptomatic HIV-infected patients, had low but significant levels of plasma α-N-acetylgalactosaminidase activity. Since a large amount (260 μg/ml) of Gc protein exists in the blood stream, a low level of the enzyme does not affect the precursor activity. Nevertheless, α-N-acetylgalactosaminidase activity was found in plasmas of all cancer and HIV-infected patients and had an inverse correlation with the precursor activity of their plasma Gc protein (Yamamoto et al., AIDS Res. Human Ret. 11:1373, 1995). Thus, increase in patient plasma α-N-acetylgalactosaminidase activity is responsible for decrease in the precursor activity of plasma Gc protein. These observations lead us to propose that plasma α-N-acetylgalactosaminidase plays a role in immunosuppression in cancer and HIV-infected/AIDS patients.

B. The Origin of Immunosuppression

The source of the plasma α-N-acetylgalactosaminidase in cancer patients appeared to be cancerous cells. High α-N-acetylgalactosaminidase activities were detected in tumor tissue homogenates of various organs, including eleven different tumor tissues including 4 lung, 3 breast, 3 colon and 1 cervix tumors, though the α-N-acetylgalactosaminidase activity varied from 15.9 to 50.8 nmoles/mg/min. Surgical removal of malignant lesions in human cancer results in subtle decrease of plasma α-N-acetylgalactosaminidase activity with concomitant increase in the precursor activity, particularly if malignant cells are localized.

Figure 2:
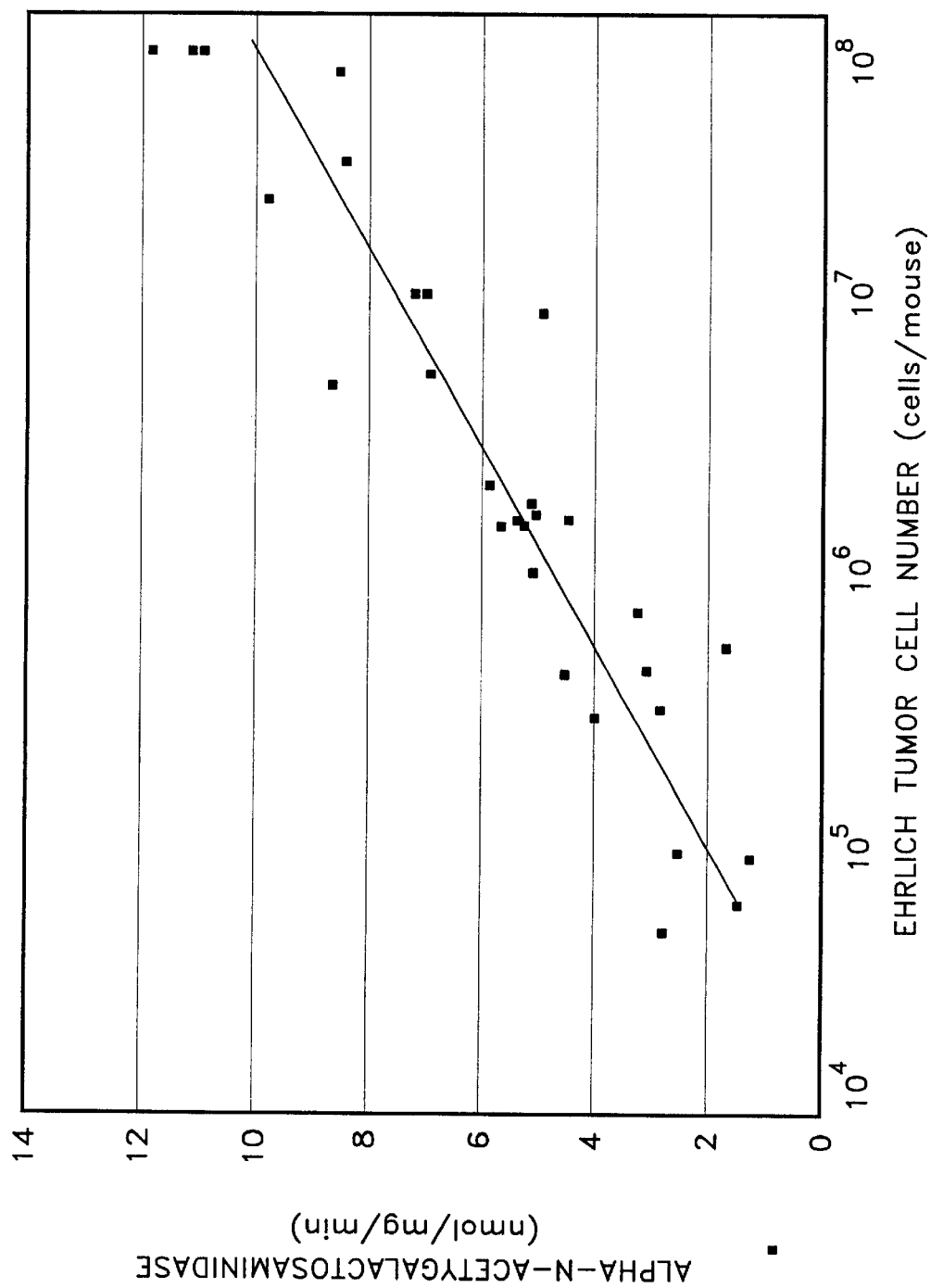
FIG. 2 shows the correlation between plasma α-N-acetylgalactosaminidase activity and tumor burden (total cell counts) in the peritoneal cavity of Ehrlich ascites tumor.

In a preclinical mouse tumor model, BALB/c mice were transplanted with $5 \times 10^5$ Ehrlich ascites tumor cells/mice into peritoneal cavity and analyzed for serum α-N-acetylgalactosaminidase activity. When plasma enzyme level were measured as transplanted Ehrlich ascites tumor grew in mouse peritoneal cavity, the enzyme activity was directly proportional to tumor burden as shown in FIG. 2. This was also confirmed with nude mouse transplanted with KB cells (human oral squamous cell carcinoma cell line). Serum α-N-acetylgalactosaminidase activity increased as tumor size (measured by weight) of the solid tumor increased. Thus, I have been using plasma α-N-acetylgalactosaminidase activity as a prognostic index to monitor the progress of therapy.

Radiation therapy of human cancer decreased plasma α-N-acetylgalactosaminidase activity with a concomitant increase of precursor activity. This implies that radiation therapy decreases the number of cancerous cells capable of secreting α-N-acetylgalactosaminidase. These results also confirmed that plasma α-N-acetylgalactosaminidase activity has an inverse correlation with the MAF precursor activity of Gc protein. Even after surgical removal of tumor lesions in cancer patients, most post-operative patients carried significant amounts of α-N-acetylgalactosaminidase activity in their blood stream. The remnant cancerous lesions in these post-operative patients cannot be detectable by any other procedures, e.g., X-ray, scintigraphy, etc. I have been using this most sensitive enzyme assay as prognostic index during the course of GcMAF therapy for treating cancer.

HIV-infected cells appeared to secrete α-N-acetylgalactosaminidase. When peripheral blood mononuclear cells (PBMC) of HIV-infected patients were cultured and treated with mitomycin as a provirus inducing agent (Sato et al., Arch. Virol. 54:333, 1977), α-N-acetylgalactosaminidase was secreted into culture media. These results led us to suggest that α-N-acetylgalactosaminidase is a virus coded product. In fact, HIV-envelope protein gp120 appears to carry the α-N-acetylgalactosaminidase activity.

C. A Defect In Macrophage Activation Cascade Manifests Osteopetrosis

An inflammation-primed macrophage activation cascade has been defined as a major process leading to the production of macrophage activating factor. Activation of other phagocytes such as osteoclasts shares the macrophage activation cascade (Yamamoto et al., J. Immunol. 152:5100, 1994). Thus, a defect in the macrophage activation cascade results in lack of activation in osteoclasts.

Autosomal recessive osteopetrosis is characterized by an excess accumulation of bone throughout the skeleton as a result of dysfunctional osteoclasts, resulting in reduced bone resorption (Marks, Clin. Orthop. 189:239, 1984). In animal models of osteopetrosis, depending on the degree of osteoclast dysfunction, marrow cavity development and tooth eruption are either delayed or more commonly absent (Marks, Am. J. Med. Genet. 34:43, 1989). In human infantile osteopetrosis, death occurs within the first decade of life usually overwhelming infection (Reeves, Pediatrics. 64:202,1979), indicating immunosuppression. Accumulated evidence suggests that deficient or dysfunctional osteoclasts in osteopetrotic animals are often accompanied by deficiencies or dysfunctions of macrophages. The studies of the present inventor on the activation of both osteoclasts and macrophages in the osteopetrotic mutations revealed that osteoclasts and macrophages can be activated by a common signaling factor, the macrophage activating factor and that a defect in β-galactosidase of B cells incapacitates the generation process of macrophage activating factor (Yamamoto et al., J. Immunol. 152:5100, 1994). Since GcMAF and its cloned derivatives bypass the function of lymphocytes and Gc protein and act directly on macrophages and osteoclasts, administration of these factors into osteopetrotic hosts should rectify the bone disorder. In fact the present inventor has recently found that four administrations of purified cloned human macrophage activating factor (GcMAFc)

(100 pg/week) to the op mutant mice beginning at birth for four weeks resulted in the activation of both macrophages and osteoclasts and subsequent resorption of the excess skeletal matrix.

D. Therapeutic Application of GcMAF and its Cloned Derivatives on Cancer

Despite defects in the macrophage activation cascade in cancer, HIV-infected and osteopetrotic patients, GcMAF bypasses the functions of lymphocytes and Gc protein and acts directly on macrophages (or osteoclasts) for activation. Macrophages have a potential to eliminate cancerous cells and HIV-infected cells when activated. When cancer patients were treated with 100 ng GcMAF/patient weekly for several months, GcMAF showed remarkable curative effects on a variety of human cancer indiscriminately.

Instead of obtaining of GcMAF from human blood source, it can be obtained from the cloned Gc protein or its small domain responsible for macrophage activation. The cloning Gc protein require an eukaryotic vector/host capable of the glycosylation of the cloned products. The Gc protein having a molecular weight of 52,000 and 458 amino acid residues) is a multi-functional protein and carries three distinct domains (Cooke and Haddad, *Endocrine Rev.*, 10:294, 1989).

Domain I interacts with vitamin D while domain III interacts with actin (Haddad et al., *Biochem.*, 31:7174, 1992). Chemically and proteolytically fragmented Gc enabled me to indicate that the smallest domain, domain III, contains an essential peptide for macrophage activation. Accordingly, I cloned both Gc protein and the entire domain III peptide, by the use of a baculovirus vector and an insect host, and treated them with the immobilized β-galactosidase and sialidase to yield potent macrophage activating factors, designated GcMAFc and CdMAF, respectively. Like GcMAF, these cloned GcMAFc and CdMAF appear to have curative effects on cancer.

E. A Potent Adjuvant Activity of GcMAF for Immunization with Antigens or Vaccines Macrophages are antigen presenting cells. Macrophages activated by GcMAF rapidly phagocytize target antigens or cells and presented the processed antigens to antibody producing cells. I observed a rapid development of a large amount of antibody secreting cells immediately (1 to 4 days) after inoculation of small amount of GcMAF (100 pg/mouse) and sheep erythrocytes (SRBC). This finding indicates that GcMAF and its cloned derivatives, GcMAFc and CdMAF, should serve as potent adjuvants for immunization and vaccination.

DESCRIPTION OF THE METHODS FOR GENE CLONING FOR MACROPHAGE ACTIVATING FACTORS

A. Cloning of the cDNA of Gc Protein Into an Insect Virus

A full length cDNA encoding the human Gc protein was isolated from a human liver cDNA library in bacteriophage λgt 11 (Clontech, Palo Alto, Calif.) by the use of pico Blue™ immunoscreening kit available from Stratagene of La Jolla, Calif. The baculoviral expression system in the insect cells takes advantages of several facts about the polyhedron protein: (a) it is expressed to very high levels in infected cells where it constitutes more than half of the total cellular protein late in the infection cycle; (b) it is nonessential for infection or replication of the virus, meaning that the recombinant virus does not require any helper function; (c) viruses lacking polyhedron gene have distinct plaque morphology from viruses containing the cloned gene; and d) unlike bacterial cells, the insect cell efficiently glycosylate the cloned gene products.

One of the beauties of this expression system is a visual screen allowing recombinant viruses to be distinguished and quantified. The polyhedron protein is produced at very high levels in the nuclei of infected cells late in the viral infection cycle. Accumulated polyhedron protein forms occlusion bodies that also contain embedded virus particles. These occlusion bodies, up to 15 μm in size, are highly retractile, giving them a bright shiny appearance that is readily visualized under a light microscope. Cells infected with recombinant viruses lack occlusion bodies. To distinguish recombinant virus from wild-type virus, the transfection supernatant (recombinant containing virus lysate) is plaqued onto a monolayer of insect cells. Plaques are then screened under a light microscope for the presence (indicative of wild-type virus) or absence (indicative of recombinant virus) of occlusion bodies.

Unlike bacterial expression systems, the baculovirus-based system is an eukaryotic expression system and thus uses many of the protein modification, processing such as glycosylation, and transport reactions present in higher eukaryotic cells. In addition, the baculoviral expression system uses a helper-independent virus that can be propagated to high titers in insect cells adapted for growth in suspension cultures, making it possible to obtain large amounts of recombinant protein with relative ease. The majority of the overproduced protein remains soluble in insect cells by contrast with the insoluble proteins often obtained from bacteria. Furthermore, the viral genome is large (130 kbp) and thus can accommodate large segments of foreign DNA. Finally, baculoviruses are noninfectious to vertebrates, and their promoters have been shown to be inactive in mammalian cells (Carbonell et al., *J. Virol.* 56:153, 1985), which gives them a possible advantage over other systems when expressing oncogenes or potentially toxic proteins.

1) Choice of Baculoviral Vector.

All available baculoviral vectors are pUC-based and confer ampicillin resistance. Each contains the polyhedron gene promoter, variable lengths of polyhedron coding sequence, and insertion site(s) for cloning the foreign gene of interest flanked by viral sequences that lie 5' to the promoter and 3' to the foreign gene insert. These flanking sequences facilitate homologous recombination between the vector and wild-type baculoviral DNA (Ausubel et al., *Current Protocols in Mol. Biol.* 1990). The major consideration when choosing the appropriate baculoviral expression vector is whether to express the recombinant as a fusion or non-fusion protein. Since glycosylation of Gc peptide requires a leader signal sequence for transfer of the peptide into the endoplasmic reticulum, the cDNA containing initiation codon (−16 Met) through the leader sequence to the +1 amino acid (leu) of the native Gc protein should be introduced to non-fusion vector with a polylinker carrying the EcoRI site, pLV1393 (Invitrogen, San Diego, Calif.).

During partial digestion of the cDNA for Gc protein in λgt11 with EcoRI enzyme, a full length Gc cDNA with EcoRI termini was isolated electrophoretically, mixed with EcoRI-cut pVL1393, and ligated with T4 ligase. This construct in correct orientation should express the entire Gc peptide, a total of 458 amino acids (FIG. 3). To obtain the correct construction, competent *E. coli* HB101 cells were transformed with pVL vector and selected for transformants on Luria broth agar plates containing ampicillin (LB/ampicillin plates). The DNA was prepared for the sequencing procedure to determine which colony contains the insert or gene with proper reading orientation, by first searching for the 3' poly A stretch. The clones with 3' ply A (from the poly A tail of mRNA) were then sequenced from the 5' end to confirm the correct orientation of the full length DNA for the Gc peptide.

2) Co-transfection of Insect Cells with the Cloned Plasmid DNA and Wild-Type Viral DNA A monolayer ($2.5 \times 10^6$ cells in each of 25-cm² flasks) of Spodoptera frugiperda (Sf9) cells was co-transfected with a cloned plasmid (vector) DNA (2 µg) and a wild-type (Ac-MNPV) baculoviral DNA (10 µg) in 950 µl transfection buffer (Ausubel et al., In Curr Protocols in Mol. Biol. 1990). When the cells were cultured for 4 or 5 days, the transfection supernatant contained recombinant viruses.

3) Identification of Recombinant Baculovirus

The co-transfection lysates were diluted $10^4$, $10^5$ or $10^6$ and plated on Sf9 cells for cultivation for 4 to 6 days. After the plaques were well formed, plaques containing occlusion-negative cells were identified at a frequency of 1.3%. Several putative recombinant viral plaques were isolated and twice re-plaqued for purification. Pure recombinant viral plaque clones were isolated.

B. Analysis of Protein of Interest from Recombinant Baculovirus

1) Preparation of Recombinant Virus Lysate

An insect cell Sf9 monolayer ($2.5 \times 10^6$ cells per 25-cm² flask) was infected with a recombinant virus clone and cultured in 5 ml GIBCO serum-free medium (from GIBCO Biochemicals, Rockville, Md.) or medium supplemented with 0.1% egg albumin to avoid contamination of serum bovine vitamin D binding protein. The culture flasks were incubated at 27° C. and monitored daily for signs of infection. After 4 to 5 days, the cells were harvested by gently dislodging them from the flask and the cells and culture medium were transferred to centrifuge tubes and centrifuged for 10 min at 1000×g, 4° C. To maximize infection for recombinant protein production, Sf9 cells were grown in a 100-ml spinner suspension culture flask with 50 ml complete medium up to about $2 \times 10^6$ cells/ml. The cells were harvested, centrifuged at 1000×g for 10 min and re-suspended in 10 to 20 ml serum-free medium containing recombinant virus at a multiplicity of infection (MOI) of 10. After 1 hour of incubation at room temperature, the infected cells were transferred to a 200-ml spinner flask containing 100 ml serum-free medium and incubated for 40 hr. More than 40% of the protein secreted was the protein of interest. The protein in the supernatant was isolated.

2) Qualitative Estimation of the Protein of Interest

Coomassie Blue staining of the SDS-polyacrylamide gel, loading 20 to 40 µg total cell protein per lane, was to estimate quantity of expressed protein. Because the samples contain cellular proteins, the recombinant protein was readily detected by comparison with uninfected cellular proteins.

3) Enzymatic Conversion of the Cloned Gc Protein to Macrophage Activating Factor (GcMAFc).

The cloned Gc protein (2 µg) with a molecular weight of 52,000 and 458 amino acid residues (FIG. 3) was isolated by electroeluter and treated with immobilized β-galactosidase and sialidase. The resultant cloned macrophage activating factor (GcMAFc) was added to mouse and human macrophages and assayed for phagocytic and superoxide generating capacity. Incubation of macrophages with 10 pg GcMAFc/ml for 3 hours resulted in a 5-fold increased phagocytic and a 15-fold increase in the superoxide generating capacity of macrophages.

C. Subcloning of a Domain Required for Macrophage Activation

I. Cloning procedure I: Non-fusion vector.

1) Cloning the Domain Responsible for Macrophage Activation (CdMAF)

The entire cDNA sequence for Gc protein in λgt11, including 76 bp of the upstream 5' flanking region and 204 bp of the 3' flanking stretch, was fragmented by EcoRI to yield four restriction fragments designated E1, 120; E2, 314; E3, 482; and E4, 748 bp, respectively. Each was cloned into the EcoRI site of the plasmid pSP65 from Promega (Madison, Wis.) by the method of Cooke and David (J. Clin. Invest., 76 2420, 1985). Although I found that a region less than one half of the domain III was found to be responsible for macrophage activation, small segments less than 40 amino acid residues cannot be expressed in the insect cells. Moreover, short peptides are rapidly degraded by proteases in human plasma, and thus are not clinically useful. Accordingly, the entire domain III (approximately 80 amino acid residues) should be subcloned into an insect virus where I anticipate the efficient production and glycosylation of the peptide in the infected cells.

2) Subcloning cDNA Fragment into the Polyhedron Gene of Baculovirus.

Figure 4:
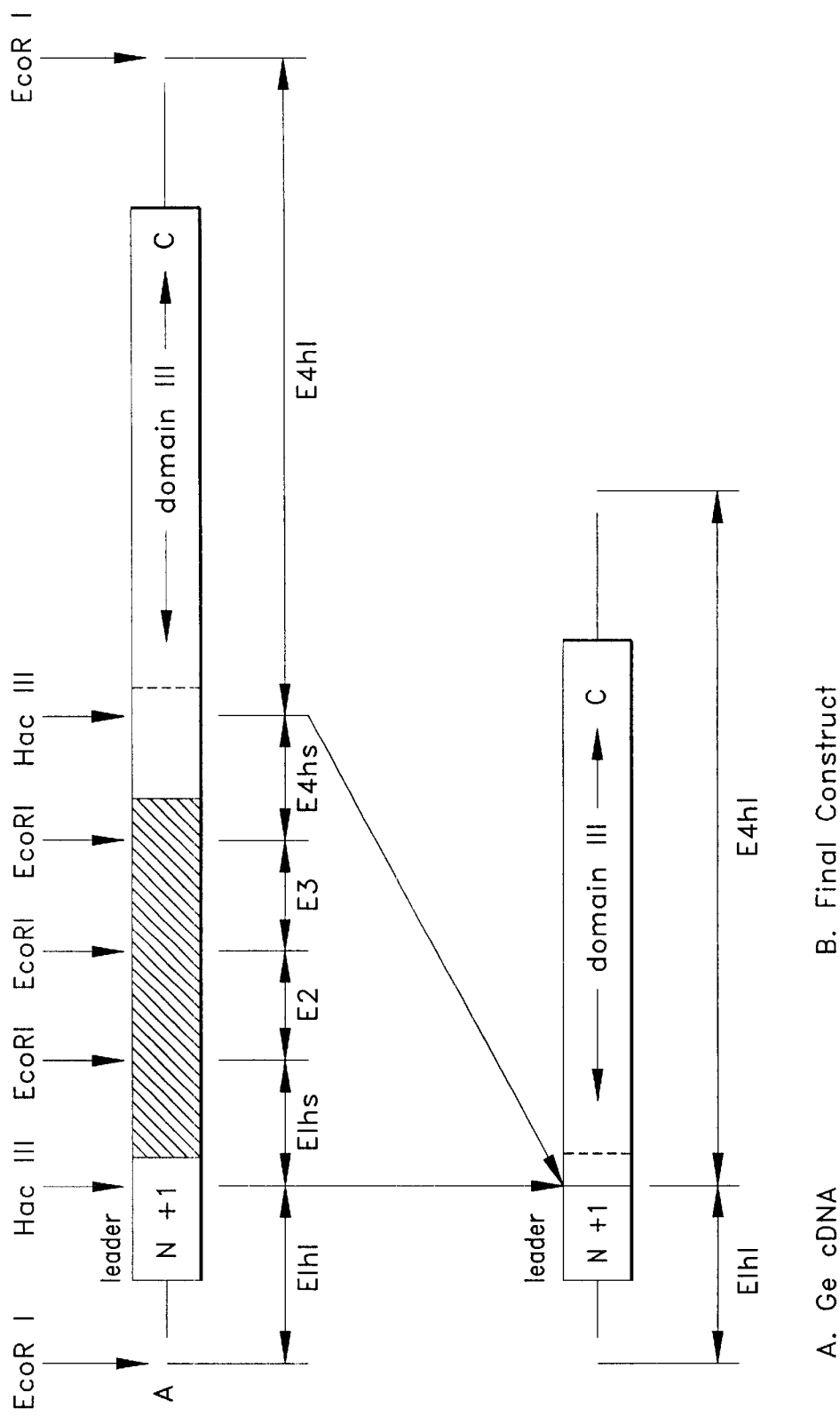
FIG. 4 shows the construction of the DNA fragment encoding the leader sequence of EcoRi fragment E1 and domain III regions of the Gc protein; A, the entire cDNA for Gc protein; B, the construct to be inserted into the non-fusion vector; the shaded area indicates the compressed regions of about 1,000 base pairs (bp).
Figure 6:
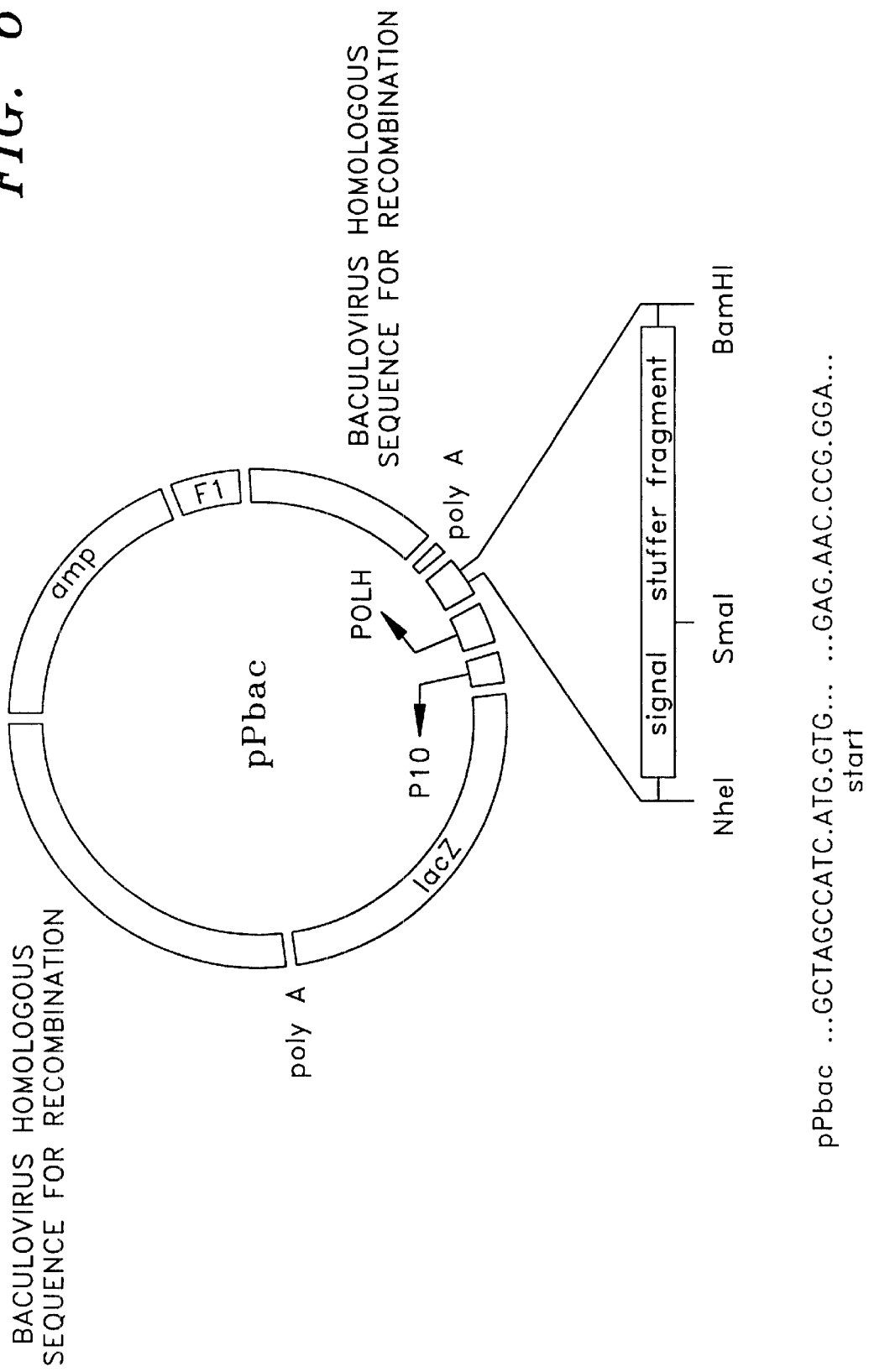
FIG. 6 shows the baculovirus fusion vector for cloning the domain III of Gc protein.
Figure 8D:
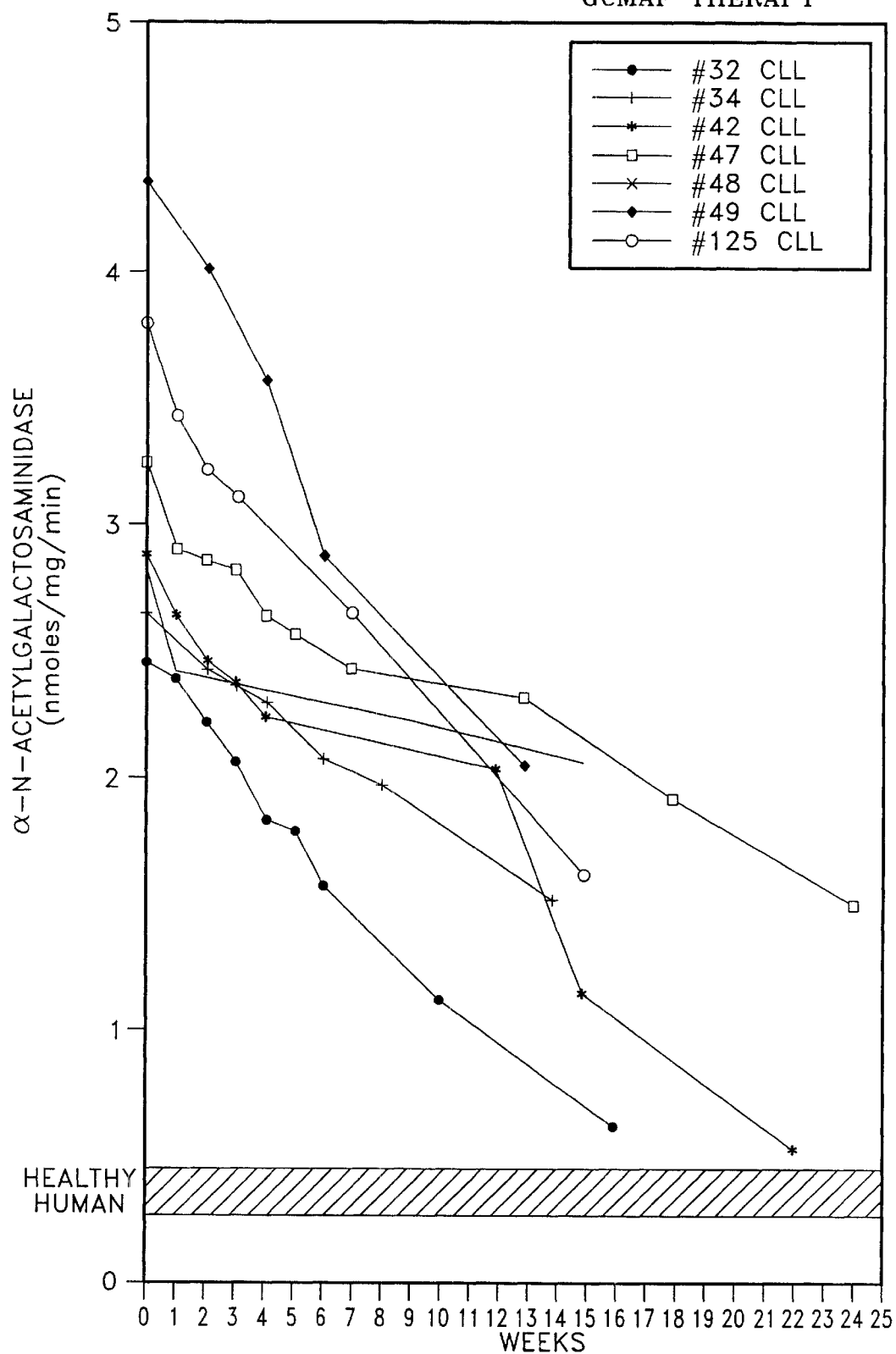
FIG. 8d shows the therapeutic effect of GcMAF in accordance with the present invention on adult persons suffering from leukemia.

Since the glycosylation of a peptide requires a leader signal sequence for transfer of the peptide into the endoplasmic reticulum, the DNA segment of E1 containing the initiation codon (−16 Met) through the leader sequence to the +1 amino acid (Leu) of the native Gc protein should be introduced into the vector. Because this segment carries the initiation codon for the Gc protein, non-fusion vector, pVL1393 (Invitrogen, San Diego, Calif.) was used. A segment containing the initiation codon-leader sequence of the cDNA clone E1 and a segment coding for 85 C-terminal amino acids (the entire domain III plus 3' non-coding stretch) of the cDNA clone E4 were ligated together and cloned into the EcoRI site of the insect virus pVL vector. To achieve this construct, both E1 and E4 DNA were fragmented with HaeIII to yield two fragments each; E1hl (87 bp), E1hs (33 bp) and E4hs (298 bp), E4hl (450 bp), respectively. Both the larger fragments E1hl and E4hl were isolated electrophoretically, mixed with EcoRI-cut pVL, and ligated with T4 ligase, as shown in FIG. 4. This construct in correct orientation should express the entire domain III, a total of 89 amino acids, including the 4 amino acids of E1hl, also referred to herein as CdMAF$_1$, as shown in FIG. 5. To obtain the correct construction, competent E. coli HB101 cells are transformed with pVL vector and selected for transformants on LB/ampicillin plates. DNA was prepared for sequencing procedures to determine which colony contains the construct with proper reading orientation by first searching for the 3' poly dA stretch. Those clones with 3' poly dA (from the poly A tail of mRNA) were then sequenced from the 5' end to confirm correct orientation of the E1hl fragment. I found that the vector contains the entire construct (domain III) in the correct orientation.

3) Isolation of Recombinant Baculovirus, Purification of the Cloned Domain Peptide (Cd) and Enzymatic Generation of the Cloned Macrophage Activating Factor (CdMAF)

Monolayers ($2.5 \times 10^6$ cells in each of 25-cm² flasks) of Spodoptera frugiperda (Sf9) cells were co-transfected with cloned plasmid DNA (2 µg) and wild-type (AcMNPV) baculoviral DNA (10 µg) in 950 µl transfection buffer. Recombinant baculovirus plaques were isolated and used for production of the Gc domain III peptide in insect cells. This cloned domain with a molecular weight (MW) of 10,000 and 89 amino acids as shown in FIG. 5, was purified electrophoretically. Two µg of the cloned domain (Cd) peptide was treated with immobilized β-galactosidase and sialidase to yield a cloned macrophage activating factor, designated as CdMAF$_1$.

II. Cloning Procedure II: Fusion Vector,

1) Cloning the Domain Responsible for Macrophage Activation (CdMAF)

A baculovirus fusion vector, pPbac vector (Stratagene, La Jolla, Calif.), contains human placental alkaline phosphatase secretory signal sequences that direct the nascent cloned peptide chain toward the secretory pathway of the cells leading to secretion into culture media. The signal sequence is cleaved off by signal-sequence peptidase as the nascent cloned peptide is channeled toward the secretory pathway of the host insect cells leading to secretion of the cloned domain (Cd) peptide. FIG. 6 depicts that the vector carries the stuffer fragment for gene substitution and lacZ gene for identification of the gene insertion.

The stuffer fragment of pPbac vector was excised by digesting the vector DNA with restriction enzymes SmaI and BamHI and was removed by electroelution. The E4 cDNA fragment of the Gc protein was digested with HaeIII and BamHI, yielding a fragment practically the same as E4hl (see FIG. 4). This fragment was mixed with the above pPbac vector and ligated with T4 ligase. This strategy not only fixes the orientation of ligation but also fuses the fragment with the reading frame. The *E. coli* DH5aF' cells were transformed with the reaction mixture. The cloned DNA insert was isolated from a number of colonies after digestion with HaeIII and BamHI. The insert was confirmed by sequencing. The sequence confirmed the correct orientation.

2) Isolation of Recombinant Baculovirus by Transfection of Sf9 Insect Cells With Wild Type Baculovirus and the Cloned DNA Insert.

For transfection of insect cells (*Spodoptera frugiperda*, Sf9), linear wild type (AcMNPV) baculoviral DNA and insectin liposomes (Invitrogen, San Diego, Calif.) have been used. Liposome-mediated transfection of insect cells is the most efficient transfection method available. For transfection to a monolayer of Sf9 cells ($2\times10^6$) in a 60 mm dish a mixture of the following was gently added:

3 μg cloned plasmid DNA

10 μl linear wild type baculovirus (AcMNPV) DNA (0.1 μg/μl)

1 ml medium

29 μl insectin liposomes

The dishes were incubated at room temperature for 4 hours with slow rocking. After transfection, the 1 ml of medium was added and incubated at 27° C. in a humidified environment for 48 hours. The resultant transfection lysate was plaque assayed. Purification of recombinant virus, isolation of the cloned domain peptide (Cd) and enzymatic generation of the cloned macrophage activating factor designated $CdMAF_2$ were described in the Cloning Procedure I. This CdMAF is composed of 94 amino acid residues as shown in FIG. 7, including 9 amino acids from the fusion vector and is referred to herein as $CdMAF_2$. Although $CdMAF_2$ has five amino acids more than the $CdMAF_1$ peptide derived from the non-fusion vector, they exhibited the same biological activities.

SUPPORTING OBSERVATIONS

A. Effects of Cloned Macrophage Activating Factors, GcMAFc and CdMAF on Cultured Phagocytes (Macrophages and Osteoclasts).

The three hour treatment of human macrophages and osteoclasts with picogram quantities (pg) of the cloned macrophage activating factors, GcMAFc and CdMAF, resulted in a greatly enhanced superoxide generating capacity of the phagocytes as shown in Table 1. The levels of the phagocyte activation are similar to those of macrophage activation by GcMAF (Yamamoto et al., *AIDS Res. Human Ret*. 11:1373,1995).

TABLE 1

Activation of phagocytes by in vitro treatment with GcMAF and its cloned derivatives.

| | Conc. pg/ml | nmole of superoxide produced/min/$10^8$ phagocytes Human macrophages* | Mouse peritoneal macrophages | Human osteoclasts |
|---|---|---|---|---|
| GcMAFc | 0 | 0.07 | 0.06 | 0.03 |
| | 10 | 3.20 | 3.46 | 2.56 |
| | 100 | 5.18 | 5.08 | 4.22 |
| CdMAF | 0 | 0.01 | 0.02 | 0.08 |
| | 10 | 2.96 | 2.87 | 2.43 |
| | 100 | 4.26 | 4.53 | 4.09 |

B. Activation of Mouse Peritoneal Macrophages by Administration of Cloned Macrophage Activating Factors, GcMAFc and CdMAF.

One day post-administration of a picogram quantity (10 and 100 pg/mouse) of GcMAFc or CdMAF to BALB/c mice, peritoneal macrophages were isolated and assayed for superoxide generating capacity. As shown in Table 2, the macrophages were efficiently activated. These results are similar to those of macrophage activation with GcMAF (Naraparaju and Yamamoto, *Immunol. Lett*. 43:143, 1994; Yamamoto et al. *AIDS Res. Human Ret*. 11:1373,1995).

TABLE 2

Activation of mouse peritoneal macrophages by administration of cloned GcMAF derivatives.

| | Dosage pg/mouse | nmole of superoxide produced/min/$10^6$ phagocytes Mouse peritoneal macrophages |
|---|---|---|
| GcMAFc | 0 | 0.05 |
| | 10 | 3.18 |
| | 100 | 5.23 |
| CdMAF | 0 | 0.03 |
| | 10 | 2.54 |
| | 100 | 4.23 |

C. Therapeutic Effects of GcMAF, GcMAFc or CdMAF on Tumor Bearing Mice and Osteopetrotic Mice.

1) Therapeutic Effects of GcMAF, GcMAFc or CdMAF on Ehrlich Ascites Tumor Bearing Mice.

When BALB/c mice were administered with GcMAF, GcMAFc or CdMAF (100 pg/mouse) and received $10^5$ Ehrlich ascites tumor cells/mouse, they survived for at least 5 weeks. All the control mice received only the ascites tumor and died in approximately 14 days. When mice were administered with an additional 100 pg GcMAF/mouse 4 days post-transplantation, the tumor cells were completely eliminated (Table 3).

When mice were transplanted with $10^5$ Ehrlich ascites tumor cells/mouse and treated twice with GcMAF, GcMAFc or CdMAF (100 pg/mouse) at 4 days and 8 days post-transplantation, all treated mouse groups survived over 65 days while the untreated 8 mouse groups all died at approximately 13 days (Groups 4 through 9 of Table 3).

TABLE 3

Therapeutic effects of GcMAF and cloned derivatives on mice bearing Ehrlich ascites tumor.

| Group | No. of mice | Post-transplantation treatment | No. of mice survived/period |
|---|---|---|---|
| Group 1. | 6 mice | untreated control | 6 mice/13 ± 3 days |
| | 10 mice | day 0 100 pg GcMAF/mouse | 10 mice/36 ± 7 days |
| Group 2. | 6 mice | untreated control | 6 mice/14 ± 4 days |
| | 10 mice | day 0 100 pg GcMAFc/mouse | 10 mice/35 ± 6 days |
| Group 3. | 6 mice | untreated control | 6 mice/14 ± 5 days |
| | 10 mice | day 0 100 pg CdMAF/mouse | 10 mice/34 ± 3 days |
| Group 4. | 8 mice | untreated control | 8 mice/15 ± 5 days |
| | 12 mice | day 0 100 pg GcMAF/mouse | |
| | | day 4 100 pg GCMAF/mouse | 12 mice/>65 days |
| Group 5. | 8 mice | untreated control | 8 mice/14 ± 5 days |
| | 12 mice | day 0 100 pg GCMAFC/mouse | |
| | | day 4 100 pg GcMAFc/mouse | 12 mice/>65 days |
| Group 6. | 8 mice | untreated control | 8 mice/14 ± 5 days |
| | 12 mice | day 0 100 pg CdMAF/mouse | |
| | | day 4 100 pg CdMAF/mouse | 12 mice/>65 days |
| Group 7. | 8 mice | untreated control | 8 mice/14 ± 4 days |
| | 8 mice | day 4 100 pg GCMAF/mouse | |
| | | day 8 100 pg GcMAF/mouse | 8 mice/>65 days |
| Group 8. | 8 mice | untreated control | 8 mice/13 ± 3 days |
| | 8 mice | day 4 100 pg GcMAFc/mouse | |
| | | day 8 100 pg GcMAFc/mouse | 8 mice/>65 days |
| Group 9. | 8 mice | untreated control | 8 mice/13 ± 5 days |
| | 8 mice | day 4 100 pg CdMAF/mouse | |
| | | day 8 100 pg CdMAF/mouse | 8 mice/>65 days |

With respect to the results of Table 3, GcMAF was administered intraperitoneally for Groups 1 through 6, and GcMAF was administered intramuscularly (systemically) for Groups 7 through 9; mice in all groups received $10^5$ tumor cells/mouse.

2) Therapeutic Effects of GcMAF and Cloned GcMAF Derivatives (GcMAFc and CdMAF) on Osteopetrotic Mice.

Administration of GcMAFc or CdMAF to new born litters of osteopetrotic op/op mouse was performed by the weekly injection of 100 picograms for four weeks beginning from a day after birth. Mice were sacrificed at 28 days. The tibiae were removed from the treated and untreated control mice, longitudinally bisected, and examined under a dissecting microscope to measure the size of the bone marrow cavity. The cavity size was expressed as a percentage of the distance between the epiphyseal plates of the tibia. The untreated mouse group formed bone marrow with 30% of the total length of tibia. The treated mouse group experienced a 20% increased bone marrow formation over that of the untreated mouse group. This increased bone marrow cavity formation is an indication of osteoclast activation and increased osteoclastic bone resorption.

D. Therapeutic Effects of GcMAF, GcMAFc and CdMAF on Human Cancer and Virus Infected Patients.

1. Cancer Patients: Therapeutic Effect of GcMAF on Prostate, Breast and Colon Cancer and Adult Leukemia Patients.

The administration of GcMAF (100 and 500 ng/human) to healthy volunteers resulted in the greatly enhanced activation of macrophages as measured by the 7-fold enhanced phagocytic capacity and the 15-fold superoxide generating capacity of macrophages. The administration of GcMAF showed no signs of any side effects to the recipients. Administration of various doses (100 pg to 10 ng/mouse) to a number of mice produced neither ill effects nor histological changes in various organs including liver, lung, kidney, spleen, brain, etc. When patients with various types of cancer were treated with GcMAF (100 ng/week), remarkable curative effects on various types of cancer were observed. The therapeutic efficacy of GcMAF on patients bearing various types of cancers was assessed by tumor specific serum α-N-acetylgalactosaminidase activity because the serum enzyme level is proportional to the total amount of cancerous cells (tumor burden). Curative effects of GcMAF on prostate, breast and colon cancer and leukemia are illustrated in FIGS. 8A to 8D. After 25 weekly administrations of 100 ng GcMAF the majority (>90%) of prostate and breast cancer patients exhibited insignificantly low levels of the serum enzyme. A similar result was also observed after 35 GcMAF administrations to colon cancer patients. Similar curative effects of GcMAF on lung, liver, stomach, brain, bladder, kidney, uterus, ovarian, larynx, esophagus, oral and skin cancers were observed. Thus, GcMAF appeared to be effective on a variety of cancers indiscriminately. However, GcMAF showed no evidence of side effects in patients after more than 6 months of therapy. This was also confirmed by blood cell counts profile, liver and kidney functions, etc.

When GcMAFc (100 ng/week) and CdMAF (100 ng/week) were administered to two prostate cancer patients each, curative effects similar to those of GcMAF were observed.

2. Virus Infected Patients

Treatment of peripheral blood macrophages of HIV-infected/AIDS patients with 100 pg GcMAF/ml resulted in a greatly enhanced macrophage activation (Yamamoto et al., AIDS Res. Human Ret. 11:1373, 1995). HIV-infected patients carry anti-HIV antibodies. HIV-infected cells express the viral antigens on the cell surface. Thus, macrophages have a potential to eliminate the infected cells via Fc-receptor mediated cell-killing/ingestion when activated.

Similarly, treatment of peripheral blood macrophages of patients chronically infected with Epstein-Barr virus (EBV) and with herpes zoster with 100 ng GcMAF/ml resulted in a greatly enhanced macrophage activation. Like HIV, EBV infects lymphocytes (B cells). Since these enveloped viruses code for α-N-acetylgalactosaminidase and infected cells secrete it into blood stream. Thus this enzyme activity in patient sera can be used as a prognostic index during therapy. After approximately 25 administrations of GcMAF (100 ng/week) to patients chronically infected with EBV and with herpes zoster, the enzyme activity decreased to that of healthy control levels. When GcMAFc (100 ng/week) and CdMAF (100 ng/week) were administered to EBV-infected patients, curative effects similar to those of GcMAF were observed.

E. Adjuvant Activities of GcMAF, GcMAFc and CdMAF for Immunization and Vaccinations.

1. Rapid Increase of the Number of Antibody Secreting Cells (PFC) In Mice after Administration of GcMAF and Sheep Erythrocytes.

BALB/c mice were inoculated with SRBC 6 hours after the intraperitoneal administration of 50 pg GcMAF/mouse. At various intervals (1–5 days) after immunization, IgM-antibody secreting cells in the spleen were determined using the Jerne plaque assay (Jerne et al., Cell-bound antibodies, Wistar Institute Press, 1963). One day post-administration of GcMAF and SRBC produced $1.35 \times 10^4$ PFC/spleen. Two days after administration of GcMAF and SRBC, the number of antibody secreting cells had increased to $8.2 \times 10^4$ PFC/spleen. By the 4th day the number of antibody secreting cells reached the maximal level (about $23.6 \times 10^4$ PFC/spleen), as shown in Table 4. In contrast, mice that received an injection of SRBC alone produced about $3.8 \times 10^4$ PFC/spleen, 4 days after SRBC-injection.

To ascertain the dose response, mice were injected with SRBC 6 hours after administration of various doses of GcMAF ranging from 1 to 50 pg/mouse. On the 4th day post-administration of GcMAF and SRBC, the number of antibody secreting cells per spleen was determined by the Jerne plaque assay. On the 4th day post-administration there was a commensurate increase in the number of plaque forming cells as the concentration of GcMAF was increased above 1 pg per mouse. At a GcMAF dose of 5, 10 and 50 pg/mouse, I detected $12.6 \times 10^4$, $20.2 \times 10^4$ and $24.3 \times 10^4$ PFC/spleen, respectively.

TABLE 4

Time course studies on development of cells secreting antibody against sheep erythrocytes (SRBC) in BALB/c mice after administration of GcMAF and SRBC[a].

| After SRBC immunization | Antibody secreting cells/spleen ($\times 10^4$) | |
| --- | --- | --- |
| (days) | SRBC only | GcMAF + SRBC |
| 1 | 0.01 ± 0.002 | 1.35 ± 0.21 |
| 2 | 0.08 ± 0.02 | 8.28 ± 1.26 |
| 3 | 1.18 ± 0.42 | 14.42 ± 2.32 |
| 4 | 3.86 ± 0.95 | 23.68 ± 6.05 |
| 5 | 2.15 ± 0.63 | 18.63 ± 3.43 |

[a]Mice were inoculated with SRBC ($10^8$ cells) 6 hr after administration of GcMAF (50 pg/mouse). The number of plaques (IgM secreting cells) was quantified microscopically on various days post-SRBC injection. The number of plaque-forming cells (PFC) per spleen is expressed as the mean value of triplicate assays ± SEM.

Without further elaboration the foregoing will so fully illustrate my invention that others may, by applying current or future knowledge, adapt the same for use under various conditions of service.

REFERENCES CITED

The following references are cited and their entire text is incorporated fully herein as are all references set forth above in the specification.

U.S. PATENT DOCUMENTS

U.S. Patent Nos. 5,177,001, 5,177,002 and 5,326,749 (Yamamoto).

OTHER PUBLICATIONS

1. Jerne, N. K., Nordin, A. A. and Henry, C., The agar plaque technique for recognizing antibody producing cells. In Amos and Koprowski (eds). Cell-bound Antibody. Wistar Institute Press, Philadelphia, Pa. (1963).
2. Sato, M., Tanaka, H., Yamada, T. and Yamamoto, N., Persistent infection of BHK/WI-2 cells with rubella virus and characterization of rubella variants. Arch. Virology 54:333–343 (1977).
3. Reeves, J. D., August, C. S., Humbert, J. R., Weston, W. L., Host defense in infantile osteopetrosis. Pediatrics. 64:202- (1979).
4. Marks, S. C., Jr., Congenital osteopetrotic mutations as probes of the origin, structure and function of osteoclasts. Clin. Orthop. 189:239- (1984).
5. Carbonell, L. F., Klowden, M. J. and Miller, L. K., Baculovirus-mediated expression of bacterial genes in dipteran and mammalian cells. J. Virol. 56:153–160 (1985).
6. Ngwenya, B. Z., and Yamamoto, N., Activation of peritoneal macrophages by lysophosphatidylcholine. Biochem. Biophys. Acta 839: 9–15 (1985).
7. Cooke, N. E. and Haddad, J. G., Vitamin D binding protein (Gc-globulin). Endocrine Rev. 10:294–307 (1989).
8. Marks, S. C., Jr., Osteoclast biology: Lessons from mammalian mutations. Am. J. Med. Genet. 34:43–54 (1989).
9. Ngwenya, B. Z. and Yamamoto, N., Contribution of lysophosphatidylcholine treated nonadherent cells to mechanism of macrophage stimulation. Proc. Soc. Exp. Biol. Med. 193:118–124 (1990).
10. Ausubel, F. A., Brent, R., Kingston, R. E., Moore, D. D., Seidman, J. G., Smith, J. A. and Struhl, K. (eds.), Expression of proteins in insect cells using baculoviral vectors. Current Protocols in Molecular Biology. Sections 16.8.1–16.11.7. Greene Publishing and Wiley-Interscience, New York (1990).
11. Yagi, F., Eckhardt, A. E. and Goldstein I. J., Glycosidases of Ehrlich ascites tumor cells and ascitic fluid-purification and substrate specificity of $\alpha$-N-acetylgalactosaminidase and $\alpha$-galactosidase: comparison with coffee bean $\alpha$-galactosidase. Arch. Biochem. Biophys. 280:61–67 (1990).
12. Yamamoto, N. and Homma, S., Vitamin $D_3$ binding protein (group-specific component, Gc) is a precursor for the macrophage activating signal from lysophosphatidylcholine-treated lymphocytes. Proc. Natl. Acad. Sci. USA. 88:8539–8543 (1991).
13. Cooke, N. E. and David, E. V., Serum vitamin D-binding protein is a third member of the albumin and alpha-fetoprotein gene family. J. Clin. Invest. 76:2420–2424 (1985).
14. Haddad, J. G., Hu, Y. Z., Kowalski, M. A., Laramore, C., Ray, K., Robzyk, P. and Cooke, N. E., Identification of the sterol- and actin-binding domains of plasma vitamin D binding protein (Gc-globulin). Biochemistry 31:7174–7181 (1992).
15. Yamamoto, N. and Kumashiro, R., Conversion of vitamin $D_3$ binding protein (Group-specific component) to a macrophage activating factor by stepwise action of $\beta$-galactosidase of B cells and sialidase of T cells. J. Immunol. 151:27–94-2902 (1993).
16. Homma, S., Yamamoto, M. and Yamamoto, N., Vitamin D binding protein (group-specific component, Gc) is the sole serum protein required for macrophage activation after treatment of peritoneal cells with lysophosphatidylcholine. Immunol. Cell Biol. 71:249–257 (1993).
17. Yamamoto, N., Kumashiro, R., Yamamoto, M., Willett, N. P. and Lindsay, D. D., Regulation of inflammation-primed activation of macrophages by two serum factors, vitamin $D_3$-binding protein and albumin. Inf. Imm. 61:5388–5391 (1993).
18. Yamamoto, N., Lindsay, D. D., Naraparaju, V. R., Irelalnd, R. A. and Popoff, S. M., A defect in the inflammation-primed macrophage activation cascade in osteopetrotic (op rats. J. Immunol. 152:5100–5107 (1994).
19. Yamamoto, N., Willett, N. P. and Lindsay, D. D., Participation of serum proteins in the inflammation-primed activation of macrophages. Inflammation. 18:311–322 (1994).
20. Naraparaju, V. R. and Yamamoto, N., Roles of $\beta$-galactosidase of B lymphocytes and sialidase of T lymphocytes in inflammation-primed activation of macrophages. Immunol. Lett. 43:143–148 (1994).

21. Yamamoto, N., Naraparaju, V. R. and Srinivasula, S. M., Structural modification of serum vitamin D₃-binding protein and immunosuppression In HIV-infected patients. AIDS Res. Human Ret. 11:1373–1378 (1995).

---

I claim:

1. A process for cloning vitamin $D_3$-binding protein domain III (Gc domain III) into baculovirus comprising the step of selecting and utilizing a baculovirus vector to clone the vitamin $D_3$-binding protein domain III (Gc domain III).

2. A process for producing a cloned macrophage activating factor (CdMAF) comprising contacting cloned domain III of vitamin $D_3$ binding protein in vitro with immobilized β-galactosidase and sialidase and obtaining the macrophage activating factor (CdMAF).

3. A macrophage activating factor (CdMAF), which is a product of the process according to claim 2.

4. A composition comprising a macrophage activating factor (CdMAF), which is a product of the process according to claim 2.

5. A cloned vitamin $D_3$-binding protein domain III (Gc domain III) consisting of an amino acid sequence of FIG. 5 (SEQ ID. NO:2)($CdMAF_1$).

6. A cloned vitamin $D_3$-binding protein domain III (Gc domain III) consisting of an amino acid sequence of FIG. 7 (SEQ ID. NO:3)($CdMAF_2$).

* * * * *